United States Patent [19]

Takahashi et al.

[11] Patent Number: 5,588,948

[45] Date of Patent: Dec. 31, 1996

[54] STEREOSCOPIC ENDOSCOPE

[75] Inventors: Susumu Takahashi, Iruma; Masao Uehara, Hachioji; Shingo Kato, Chofu; Atsushi Kidawara, Tachikawa; Katsuyuki Saito, Hachioji; Masahito Goto, Saitama-ken; Wataru Ohno, Hachioji; Iwao Kanamori, Yokohama; Toyoharu Hanzawa, Fuchu; Kenji Yoshino, Hachioji; Akio Nakada, Hachioji; Akihiro Taguchi, Hachioji; Nobuaki Akui, Hino; Hitoshi Karasawa, Hachioji; Toshihiko Hashiguchi, Sagamihara; Akihiko Mochida, Hachioji; Takashi Fukaya, Hachioji; Shinji Yamashita, Hachioji; Akira Murata, Hino; Hideki Koyanagi, Hachioji; Keisuke Saito, Fuchu, all of Japan

[73] Assignee: Olympus Optical Co. Ltd., Tokyo, Japan

[21] Appl. No.: 122,303

[22] Filed: Sep. 17, 1993

[30] Foreign Application Priority Data

Feb. 17, 1993 [JP] Japan ................................. 5-028278

[51] Int. Cl.$^6$ ............................. A61B 1/04; H04N 13/00
[52] U.S. Cl. ............................. 600/111; 348/45; 600/117; 600/137; 600/173
[58] Field of Search ...................... 128/3–10; 348/45, 348/49, 50, 56, 57; 600/111, 166, 137, 117, 173

[56] References Cited

U.S. PATENT DOCUMENTS

| | | | |
|---|---|---|---|
| 3,251,933 | 5/1966 | Beste | 348/49 |
| 4,061,135 | 12/1977 | Widraw et al. | 128/6 |
| 4,862,873 | 9/1989 | Yajima et al. | 128/6 |
| 4,877,307 | 10/1989 | Kalmanash | 348/57 |
| 4,884,876 | 12/1989 | Lipton et al. | 348/56 |
| 5,222,477 | 6/1993 | Lia | 128/6 |

FOREIGN PATENT DOCUMENTS

| | | | |
|---|---|---|---|
| 2618663 | 2/1989 | France | 128/6 |
| 2919678 | 11/1980 | Germany . | |
| 9013254 | 4/1990 | Germany | 600/137 |
| 57-69839 | 4/1982 | Japan . | |
| 4090743 | 3/1992 | Japan | 128/6 |
| 1318970 | 6/1987 | U.S.S.R. | 128/6 |

Primary Examiner—Richard J. Apley
Assistant Examiner—John P. Leubecker
Attorney, Agent, or Firm— Armstrong, Westerman, Hattori, McLeland & Naughton

[57] ABSTRACT

A stereoscopic endoscope including an objective lens system for forming an image of an object which objective lens system is arranged at the front end of an inserting section and has a single optical axis; an image transmission device coaxially arranged with the objective lens system and adapted to transmit the image formed by the objective lens system; a pupil dividing device for dividing the image transmitted through the objective lens system and the image transmission device so as to obtain left and right images of the object; an image sensing device for picking up the left and right images obtained by the pupil dividing device; a first support structure containing-at least the objective lens system; and a second support structure containing at least the pupil dividing device and the image sensing device, wherein the first and second support structures are rotatable relative to each other around an axis extending along the longitudinal dimension of the endoscope.

14 Claims, 12 Drawing Sheets

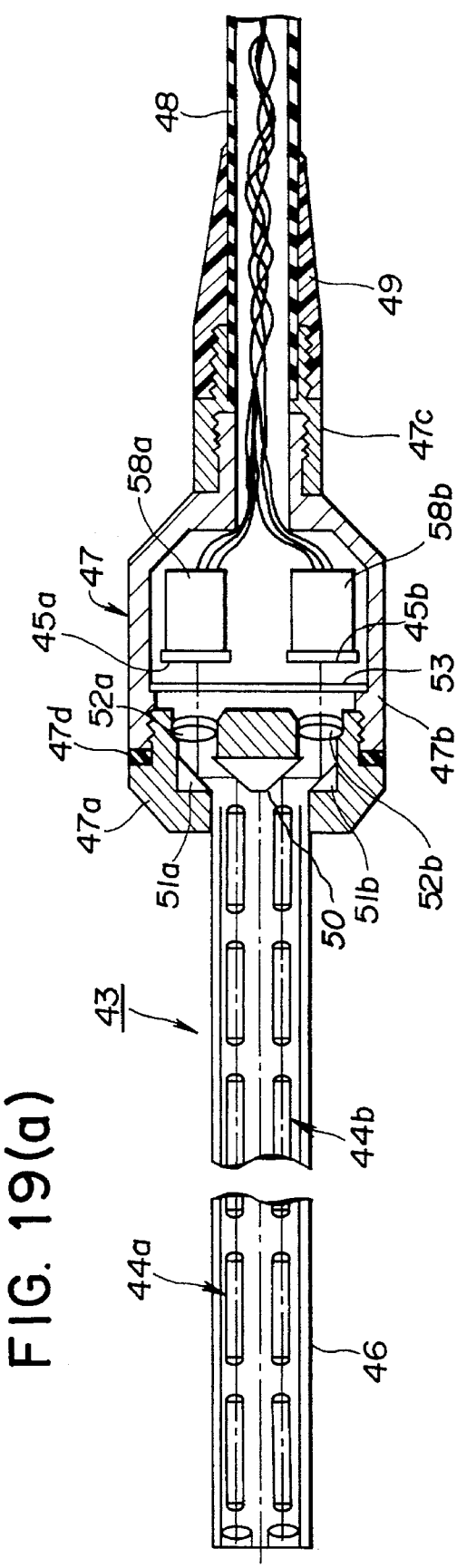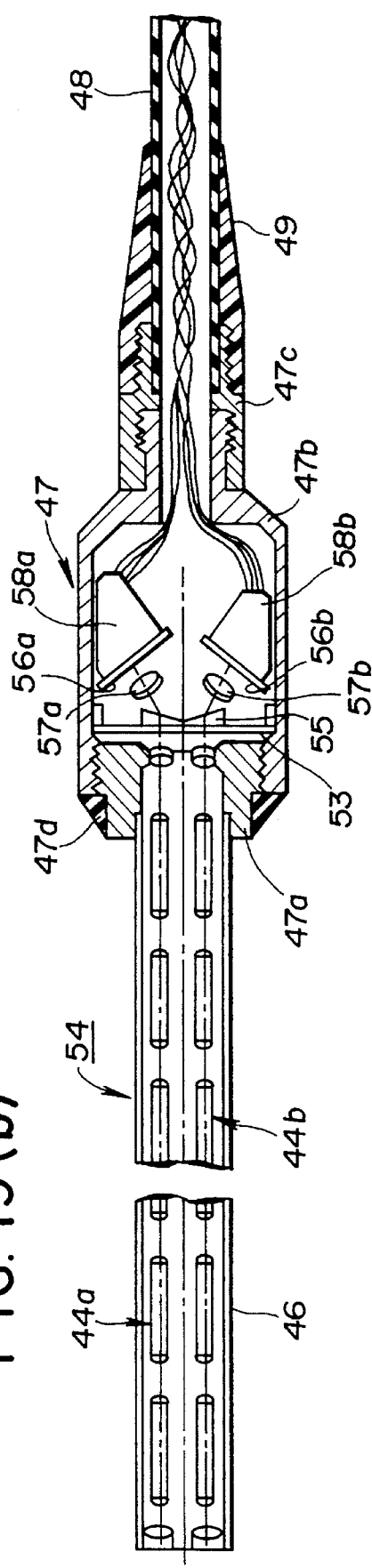
FIG. 19(a)
FIG. 19(b)

STEREOSCOPIC ENDOSCOPE

BACKGROUND OF THE INVENTION

1. Field of the Invention

The present invention relates to a stereoscopic endoscope which is used for stereoscopic observation of objects.

2. Description of the Related Art

In recent years, endoscopes for medical use, which enable the interior of a body cavity to be observed by inserting a long thin inserting section into the body cavity, have been widely used. Such an endoscope makes it possible not only to observe the interior of the body cavity but also to perform various types of medical care and treatment by using a treating instrument that is inserted into an instrument channel provided in the endoscope. Apart from this, endoscopes for industrial use are being used to observe or inspect flaws, corrosions, etc. inside the piping in boilers, chemical plants or the like, or inside the engines of automobiles, airplanes, etc.

Such endoscopes are divided into two types based on the relative hardness of the inserting section: elastic type endoscopes whose inserting section is elastic so that it can be inserted into the body cavity, which is full of twists and turns, from the oral cavity, etc.; and rigid type endoscopes whose inserting section is made rigid so as to be linearly inserted toward the section of the object to be observed.

A flexible image guide fiber is used as the optical image transmission means of the elastic type endoscope. In the rigid type endoscope, which has a rigid inserting section, a relay optical system is used as the image transmission means.

Further, endoscopes may be divided into two types based on the means of observation used: optical endoscopes with which the image is directly observed by the naked eye; and electronic endoscopes which use a solid-state image sensing device, such as a CCD (charge-coupled device), as the imaging means.

The above-mentioned conventional endoscopes have a problem in that the image thereby obtained during the observation of the interior of the body cavity is mostly a planar image having no depth. Thus, in endoscopic observation, it is rather difficult to observe the minute surface irregularities of the inner wall of the body cavity, which surface irregularities are an important diagnostic index.

To cope with this problem, stereoscopic endoscopes which make it possible to observe the minute surface irregularities of the inner wall of the body cavity have been proposed.

Japanese Patent Laid-Open No. 57-69839 discloses a stereoscopic endoscope in which eyepieces are provided at the ocular end of a pair of image guides arranged inside the inserting section, and objective lenses are provided at the other end thereof on the front-end side of the inserting section, so as to enable the interior of the body cavity to be stereoscopically observed. With this stereoscopic endoscope, it is possible to stereoscopically observe the inner wall surface of an object by adjusting the angle of convergence made by the point of observation and the pair of objective lenses in such a way as to enable stereoscopic observation. This stereoscopic endoscope is applied to an elastic type endoscope.

In a rigid type endoscope which enables an object to be stereoscopically observed, a pair of relay optical systems are arranged in parallel inside the inserting section of the endoscope, the images respectively obtained by these relay optical systems being picked up by image sensing devices such as CCDs. In this stereoscopic endoscope, electric signals representing the images formed on the image sensing devices are converted into image signals, which are displayed on a monitor, thereby making it possible to perform stereoscopic observation.

U.S. Pat. No. 4,924,835 discloses a stereoscopic endoscope which includes a pair of light transmission devices and shutters corresponding to the pair of light transmission devices, wherein the images respectively obtained by the transmission devices are alternately shaded by the shutters, thereby enabling an object to be stereoscopically observed.

Thus, in these stereoscopic endoscopes, stereoscopic observation is made possible by obtaining left and right images of the object through use of a pair of optical systems, a pair of CCDs, etc.

In the stereoscopic endoscope of the type which is provided with a pair of CCDs, the vertical dimension (the top-to-bottom relationship) of the image is determined by the position of the CCDs. As a result, the top-to-bottom relationship of the image as displayed on the monitor does not always agree with that of the monitor. Therefore, when the endoscope for observing the interior of the body cavity is rotated around the optical axis of the endoscope, the orientation of the CCDs inside the inserting section varies to change the visual-field direction, so that the image displayed on the monitor turns upon the rotation of the endoscope, resulting in there being a disparity between the top-to-bottom relationship of the monitor and that of the image.

Thus, the operator cannot immediately understand the positional relationship between the endoscope and the interior of the body cavity by glancing at the image displayed on the monitor, so that it is rather difficult to set, for example, the treating instrument, inserted through the instrument channel of the endoscope, quickly and correctly at a desired position.

SUMMARY OF THE INVENTION

It is an object of the present invention to provide a stereoscopic endoscope which is capable of compensating for the turning of an image resulting from the rotation of the endoscope around its optical axis so as to correct the top-to-bottom relationship of the image displayed on the monitor screen so that it is in conformity with the top-to-bottom relationship of the CCDs.

Another object of the present invention is to provide a stereoscopic endoscope which is capable of automatically correcting the vertical dimension of an image displayed on the monitor screen so that it is always in correspondence with the top-to-bottom relationship of the CCDs, even when the endoscope is rotated around its optical axis.

Still another object of the present invention is to provide a stereoscopic endoscope in which the diameter of the endoscope inserting section is reduced so as to mitigate the pain of the patient.

Briefly, the stereoscopic endoscope of the present invention comprises: an objective lens system for forming an image of an object which objective lens system is arranged at the front end of an inserting section and has a single optical axis; image transmission means coaxially arranged with the objective lens system and adapted to transmit the image formed by the objective lens system; pupil dividing means for dividing the image transmitted through the objective lens system and the image transmission means so as to obtain left and right images of the object; image sensing means for picking up the left and right images obtained by the pupil dividing means; first support means containing at least the objective lens system; and second support means containing at least the pupil dividing means and the image sensing means, wherein the first and second support means are rotatable relative to each other around an axis extending along the longitudinal dimension of the endoscope.

Other features and advantages of the present invention will become sufficiently apparent from the following description.

BRIEF DESCRIPTION OF THE DRAWINGS

FIGS. 3 through 6 are drawings related to a second embodiment of the present invention, of which FIG. 3 shows the construction of a controller in a stereoscopic rigid-type endoscope according to a second embodiment of the present invention;

FIG. 4 illustrates a pupil dividing means (shutter) in the second embodiment;

FIG. 5 shows the pupil dividing shutter of FIG. 4;

FIG. 6 illustrates shutter positions of the pupil dividing shutter of FIG. 5;

FIGS. 7 through 9 are drawings related to a third embodiment of the present invention, of which FIG. 7 shows the construction of a stereoscopic oblique-view-type endoscope according to the third embodiment;

FIG. 8 shows a pupil dividing shutter in the construction of FIG. 7;

FIG. 9 illustrates shutter positions of the pupil dividing shutter of FIG. 8;

FIGS. 19(a) and 19(b) shows a stereoscopic rigid-type endoscope in which the inserting section is detachable with respect to the operating/holding section.

DETAILED DESCRIPTION OF THE PREFERRED EMBODIMENTS

Figure 1:
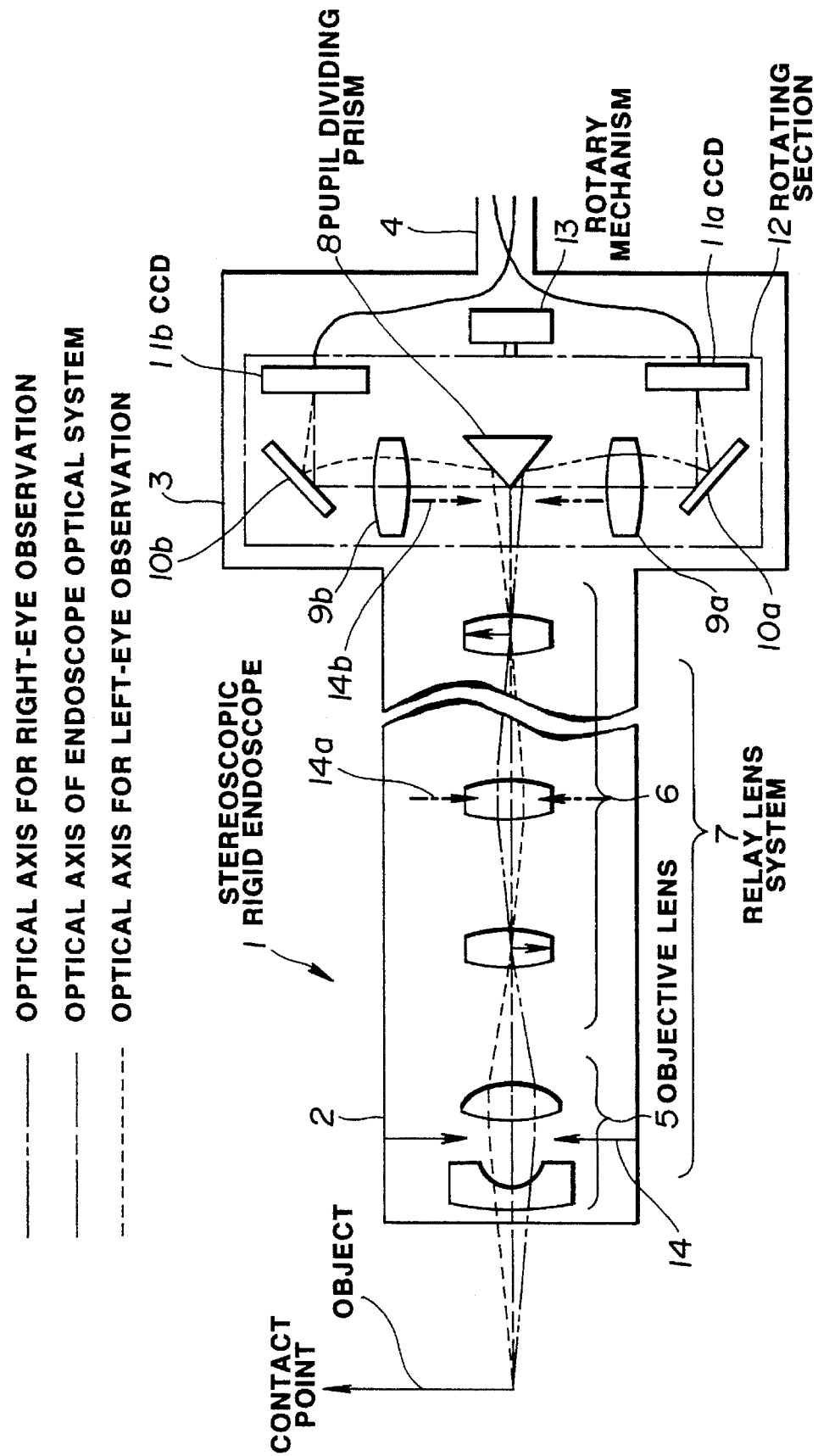
FIG. 1 shows the construction of a stereoscopic rigid-type endoscope according to a first embodiment of the present invention.
Figure 2:
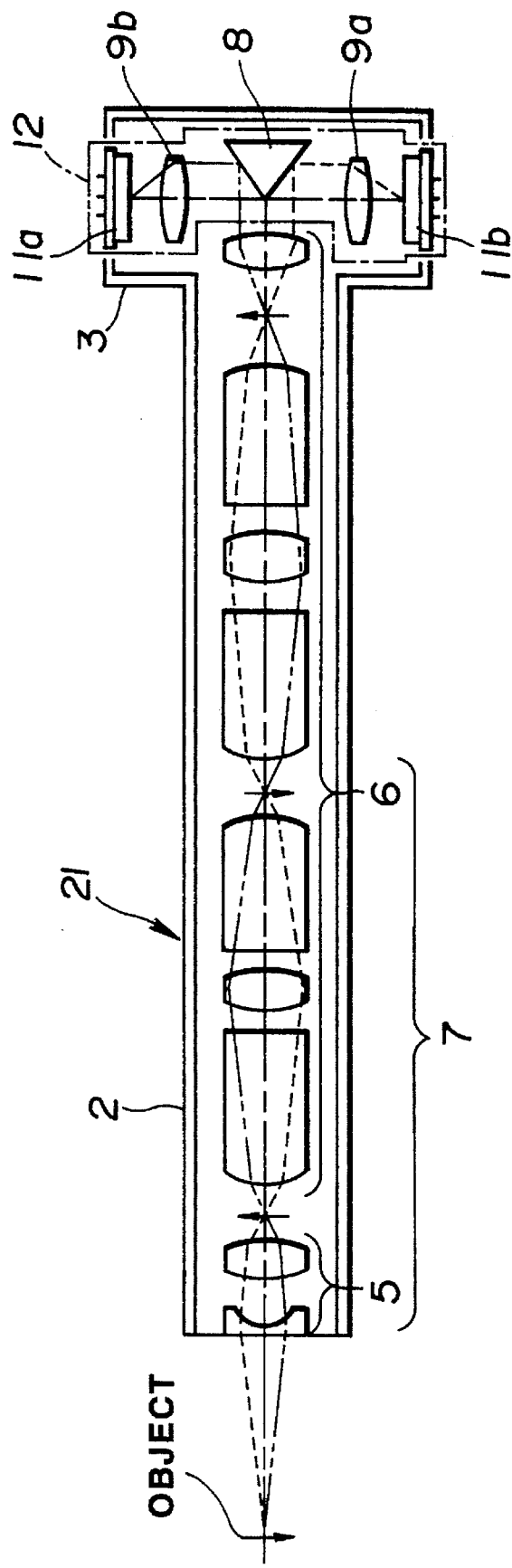
FIG. 2 shows the construction of another stereoscopic rigid-type endoscope according to the first embodiment.

A stereoscopic rigid-type endoscope according to the first embodiment of the present invention will now be described with reference to FIG. 1.

A stereoscopic rigid-type endoscope 1, shown in the drawing, is an endoscope for stereoscopic observation of an object inside the body cavity, and includes a rigid inserting section 2 and an operating/holding section 3 having a relatively large diameter and connected with the inserting section 2. A cable 4 connected to a controller extends from the rear end of the operating/holding section 3.

In the inserting section 2 of the stereoscopic rigid-type endoscope 1, an objective lens system 5 and a relay lens section 6 are arranged along an optical axis, in that order from the front end, to form a relay lens system 7, which is supported by a first support means. The objective lens system 5 is composed of a plurality of lenses, and forms an image of the object at the front end of the relay lens section 6, which is an image transmission means composed of a plurality of lens groups. This image is transmitted through the lens groups to a pupil dividing means arranged in the operating/holding section 3. In this embodiment, the pupil dividing means consists of a pupil dividing prism 8.

The pupil dividing prism 8 divides the image, transmitted through the relay lens system 7, into left and right images. For this purpose, the pupil dividing prism 8 is formed, for example, as a triangular prism, which is secured in position in such a way that its apex is in the optical axis of the relay lens system 7 and the two reflection surfaces thereof are at an angle of 45° with respect to the optical axis.

Thus, the image, transmitted through the relay lens system 7 to impinge upon the pupil dividing prism 8, is reflected in two directions, each perpendicular to the optical axis, by the two reflection surfaces so as to be divided into left and right images.

The left image, obtained by the pupil dividing prism 8, is transmitted through an image forming lens 9a and reflected by a mirror 10a to be formed on a CCD 11a, which constitutes the imaging means for the left image. An electric signal representing the left image thus formed on the CCD 11a is supplied to the controller. Similarly, the right image, obtained by the dividing action of the pupil dividing prism 8, is transmitted through an image forming lens 9b and reflected by a mirror 10b to be formed on a CCD 11b, which constitutes the imaging means for the right image. An electric signal representing the right image, formed on the CCD 11b, is likewise supplied to the controller.

The pupil dividing prism 8, the image forming lenses 9a and 9b, the mirrors 10a and 10b, and the CCDs 11a and 11b are secured to a rotating section 12, which constitutes a second support means rotating within the operating/holding section 3, which is substantially cylindrical. A rotary mechanism 13, such as a motor, is provided as the rotating means inside the rotating section 12, which is rotated, by the driving force of the rotary mechanism 13, around an axis extending along the longitudinal dimension of the endoscope.

Provided between the plurality of lenses constituting the objective lens system 5 is a pupil section 14, which is indicated by opposed arrows. By controlling the opening/closing of the pupil section 14, the pupil range of the objective lens system 5 varies. It is also possible for the pupil section 14 to be arranged at one of the positions indicated by dashed lines 14a and 14b.

Further, an optical system for illuminating the object to be observed is provided inside the stereoscopic rigid-type endoscope 1.

The above-mentioned controller controls the driving of the CCDs 11a and 11b, the rotation of the rotary mechanism 13, the amount of opening/closing of the pupil section 14, the amount of light supplied to the illumination optical system, etc.

The operation of the stereoscopic rigid-type endoscope 1, constructed as described above, will be illustrated.

As shown in FIG. 1, the image is transmitted through the objective lens 5 and formed at the front end of the relay lens section 6, in which it is divided once or more into right and left images at relay positions. In order that the left image incident upon the left side of the pupil section 14 of the objective lens system 5 may be observed with the left eye, and the right image incident upon the right side of the pupil section 14 with the right eye, the pupil dividing prism 8 divides the image into left and right images with respect to the relay lens optical axis. The divided images are transmitted by way of the image forming lenses 9a and 9b and the reflection mirrors 10a and 10b to be formed on the CCDs 11a and 11b, respectively.

The electric signals representing the images formed on the CCDs 11a and 11b undergo signal processing in the controller such that the left and right images are alternately displayed, for example, thirty times a minute on a monitor screen. By viewing the monitor screen through shaded glasses, it is possible for the viewer to stereoscopically observe the image displayed on the monitor.

The left and right lenses of the shaded glasses are alternately shaded in synchronism with the alternate display of the left and right images on the monitor screen, making it possible for the observer viewing the monitor screen to obtain an image with stereoscopic depth due to the after-image effect of the shaded glasses.

Assuming that the dimension perpendicular to the plane of FIG. 1 is the vertical dimension of the stereoscopic rigid-type endoscope 1, and that the vertical dimension of the endoscope 1 inserted into the body cavity coincides with the vertical dimension of the body cavity, the image can be displayed on the monitor screen with the top-to-bottom relationship of the endoscopic image matched with that of the monitor screen by keeping the rotating section 12 stationary.

When the vertical dimension of the endoscope has changed during observation, causing a disparity between the top-to-bottom relationship of the endoscopic image as displayed on the monitor screen and the top-to-bottom relationship of the monitor screen, only the rotating section 12 is rotated by the rotary mechanism 13 by an amount corresponding to this disparity, without rotating the endoscope itself, whereby the top-to-bottom relationship of the endoscopic image displayed on the monitor screen is made coincident with that of the monitor screen.

Since the relay lens system and the pupil dividing prism are arranged along the same optical axis, it is possible to freely change the direction of stereoscopic viewing with respect to the optical axis by rotating the rotating section alone.

In this way, it is possible for the operator to make the vertical dimension of the image displayed on the monitor screen coincident with the top-to-bottom relationship of the endoscope. Thus, the positional relationship inside the body cavity can be immediately understood by glancing at the monitor screen, so that the treating instrument, etc. can be operated quickly and correctly, thereby substantially improving the spotting performance thereof.

Further, since the components from the relay lens system to the pupil dividing prism are formed as an optical system with a single optical axis, the diameter of the inserting section can be reduced as compared with that of a stereoscopic endoscope in which an optical system having two optical axes is arranged inside the inserting section.

Further, by removing the rotating section and the rotary mechanism from the above-described construction, an inexpensive stereoscopic endoscope can be obtained which, though incapable of coping with any disparity in the positional relationship between the endoscope and the image displayed on the monitor screen, has an inserting section with a reduced diameter; and there is only a remote possibility that there will be a disparity between the left and right images.

The image sensing system of this embodiment is applicable to both color-frame-sequential type and simultaneous-type endoscopes.

The left and right images may be simultaneously displayed on the monitor, instead of being alternately displayed as described above.

Further, it is also possible to provide three or more of the above-mentioned pupil dividing means, choosing two of them for stereoscopic observation. In that case, the number of image forming lenses and CCDs arranged in the operating/holding section are made coincident with the number of divisions to be effected, resulting in an increase in the number of parts. However, by combining such a construction with the rotating means, a positional disparity can be quickly coped with.

Also, instead of using an image sensing means consisting of a solid-state image sensing device such as a CCD, eyepieces may be provided, thereby making it possible to stereoscopically observe the image with the naked eye.

The second embodiment of the present invention will now be described with reference to FIGS. 3 through 6.

Figure 3:
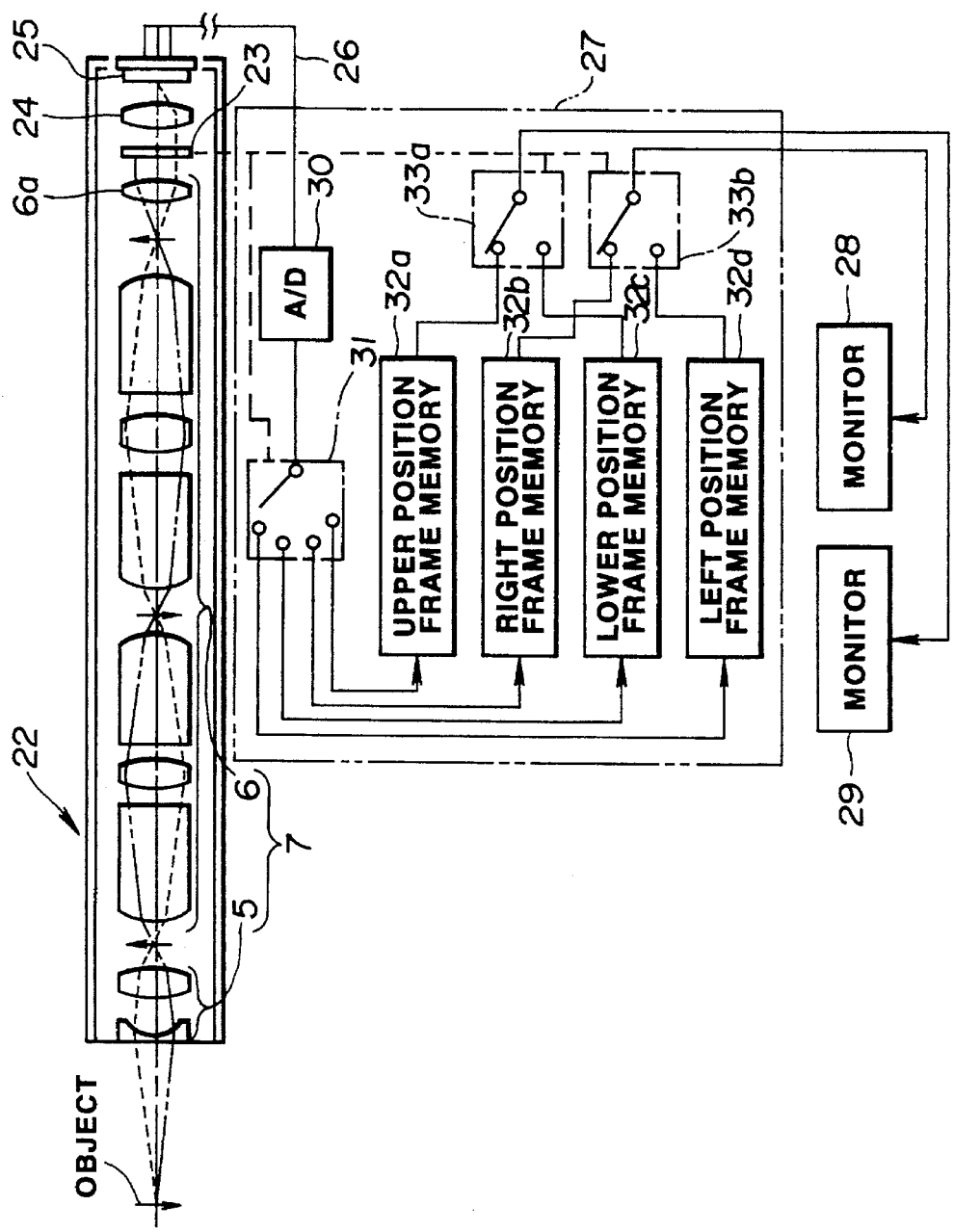

FIG. 3 shows a stereoscopic rigid-type endoscope 22 according to the second embodiment, in which, in addition to the relay lens system of the first embodiment, another optical system is provided behind it, the two systems together constituting a single image forming optical system. Further, this embodiment uses only one image sensing device. Thus, to obtain images having parallax, a pupil dividing shutter is provided as the pupil dividing means. This pupil dividing shutter selectively makes different regions of the pupil in the image forming optical system transmittable. Here, the components which are the same as those of the first embodiment are referred to by the same reference numerals, and a description of such components will be omitted.

Figure 4:
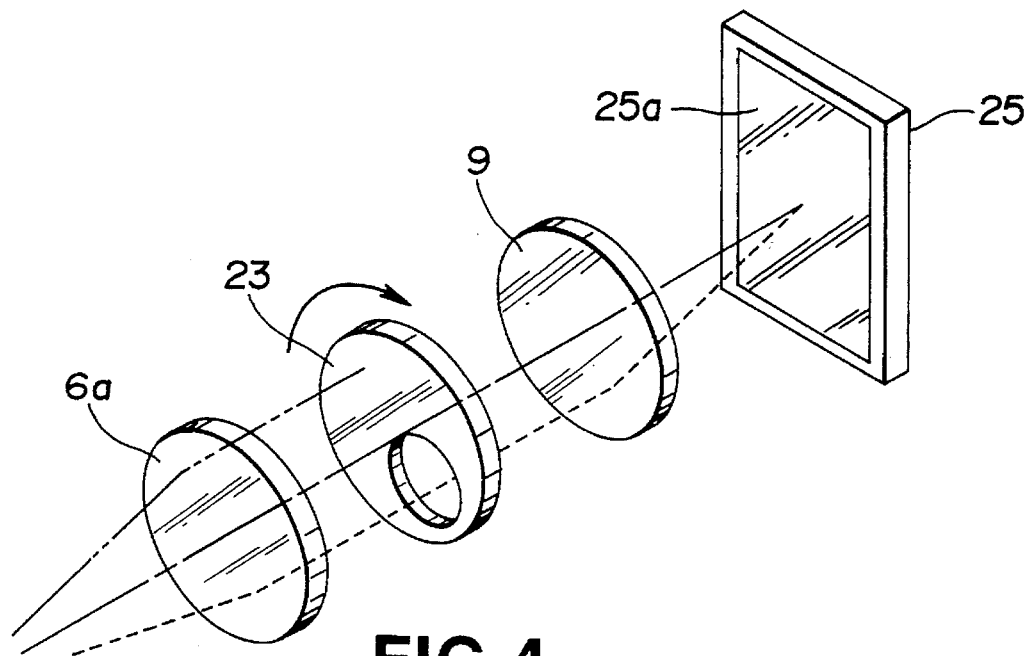

As shown in FIG. 3, arranged in the stereoscopic rigid-type endoscope 22 are a pupil dividing shutter 23, an image forming lens 24, and a CCD 25, in the order shown in FIG. 4, behind a lens 6a, which is located at the rearmost end of the relay lens section 6.

As shown in FIG. 4, the pupil dividing shutter 23 is formed as a disc having a circular shutter hole 23a to provide parallax. The central axis of the disc forming the pupil dividing shutter 23 coincides with the optical axis of the relay lens system 7, the pupil dividing shutter 23 being rotatable around this central axis. The parallax provided by the shutter 23 increases in proportion to the distance between the central axis and the shutter hole 23a formed in the pupil dividing shutter 23.

The image forming lens 24 is arranged behind the pupil dividing shutter 23 and coincides with the the optical axis of the relay lens system 7. It forms only those images of the object which have been transmitted through the shutter hole 23a, on the image area 25a of the CCD 25. Electric signals representing the images formed on the CCD 25 are supplied through a signal line 26 to a controller 27.

Figure 5:
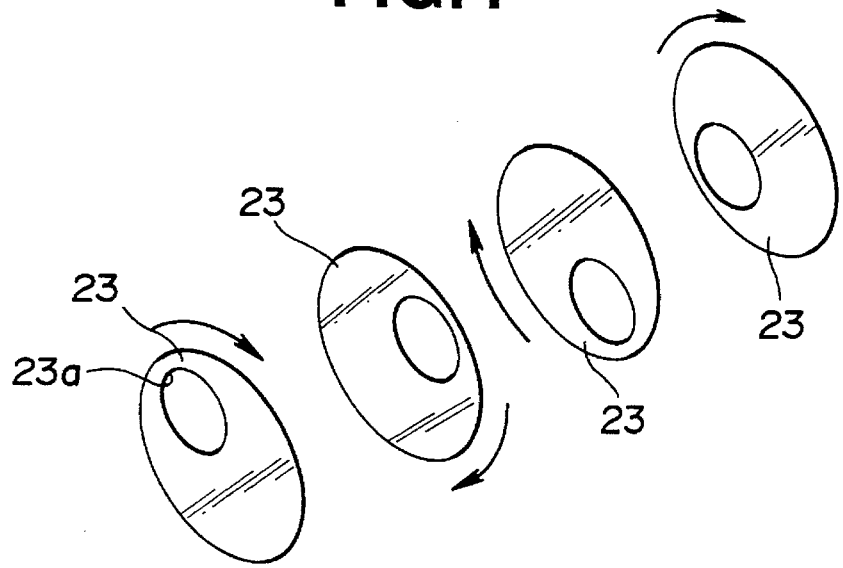
Figure 6:
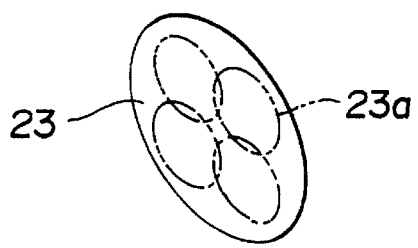

As shown in FIG. 5, images of the object are formed on the CCD 25 when the shutter hole 23 passes upper, right, lower and left shutter positions upon rotation of the pupil dividing shutter 23 around its central axis. That is, the image sensing by the CCD 25 is effected each time the shutter hole 23a passes one of the four shutter positions: the upper, lower, left and bottom positions, as shown in FIG. 6.

Light transmitted through the shutter hole at the upper, lower, left and right shutter positions forms upper, lower, left and right images, respectively, on the CCD 25. The thus formed images correspond to incident images -obtained by effecting pupil division into upper, lower, left and right sections in the relay lens system 7. Accordingly, parallax is generated between the upper and lower images and between the left and right images.

In the controller 27, the electric signals supplied from the CCD 25 are subjected to signal processing and then output to monitors 28 and 29 to display images which make stereoscopic observation possible.

The electric signals output from the CCD 25 are A/D-converted by an A/D converter 30 in the controller 27, and transmitted through a switch 31 operating in synchronism with the change in position of the shutter hole 23a to be sequentially stored in an upper frame memory 32a, a right frame memory 32b, a lower frame memory 32c, and a left frame memory 32d, which correspond to the upper, right, lower and left positions, respectively, of the shutter hole 23a.

Here, reading from each frame memory will be described.

The image signals stored in the upper frame memory 32a and those stored in the lower frame memory 32c are read through a switch 33a as A-field image signals and C-field image signals, respectively, and then A-field and C-field images are alternately displayed on the monitor 28. Likewise, the image signals stored in the right frame memory 32b and those stored in the left frame memory 32d are read through a switch 33b to be alternately displayed on the monitor 29 as B-field and D-field images, respectively.

The writing and reading of signals to and from the frame memories 32a, 32b, 32c and 33d and the operation of the switches 31, 33a and 33b are controlled through the rotation of the pupil dividing shutter 23.

By thus using the stereoscopic rigid-type endoscope with the controller described above, the operator can simultaneously observe stereoscopic images having an upper/lower and left/right parallax through two monitors.

In the case of the stereoscopic endoscope constructed as described above, the simultaneous-type image sensing system is more easily applicable from the viewpoint of construction. When applying the color-frame-sequential image sensing system to this endoscope, it is necessary to synchronize the color illumination at triple the rotating speed of the pupil dividing shutter, or to effect three-color image sensing with three rotations of the pupil dividing shutter. In the latter case, the frame memory capacity must be three times larger.

For signal processing, the construction of either the upper/lower or the left/right system of the controller shown in FIG. 3 suffices.

Figure 8:
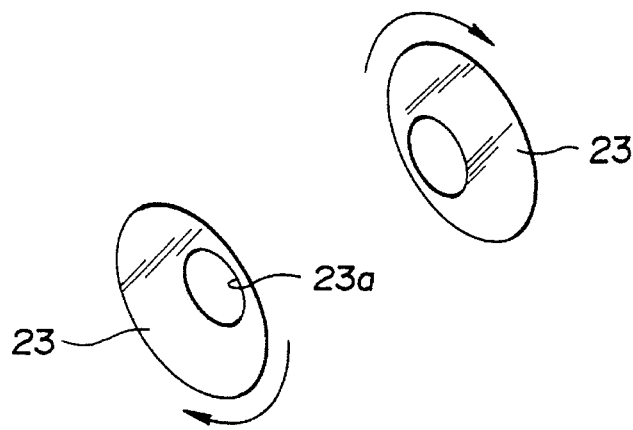
Figure 9:
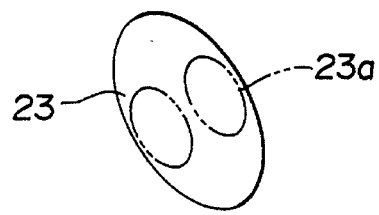

Next, the third embodiment of the stereoscopic endoscope of the present invention will be described with reference to FIGS. 7 through 9.

In a stereoscopic rigid-type endoscope 22 according to the third embodiment, the incident image of an object is divided into right and left images, as in the second embodiment, by a pupil dividing shutter 23. In the rotating section 12, in which the pupil dividing shutter 23 and a CCD 25 are arranged and which constitutes the second support means, a weight 61 or the like is secured in position so as to keep the rotating section 12 stationary, whereby any rotation of the monitor image upon rotation of the endoscope is automatically corrected. The stereoscopic endoscope of this embodiment is of an oblique-view type which has a visual field obliquely ahead of the front end of the inserting section.

Figure 7:
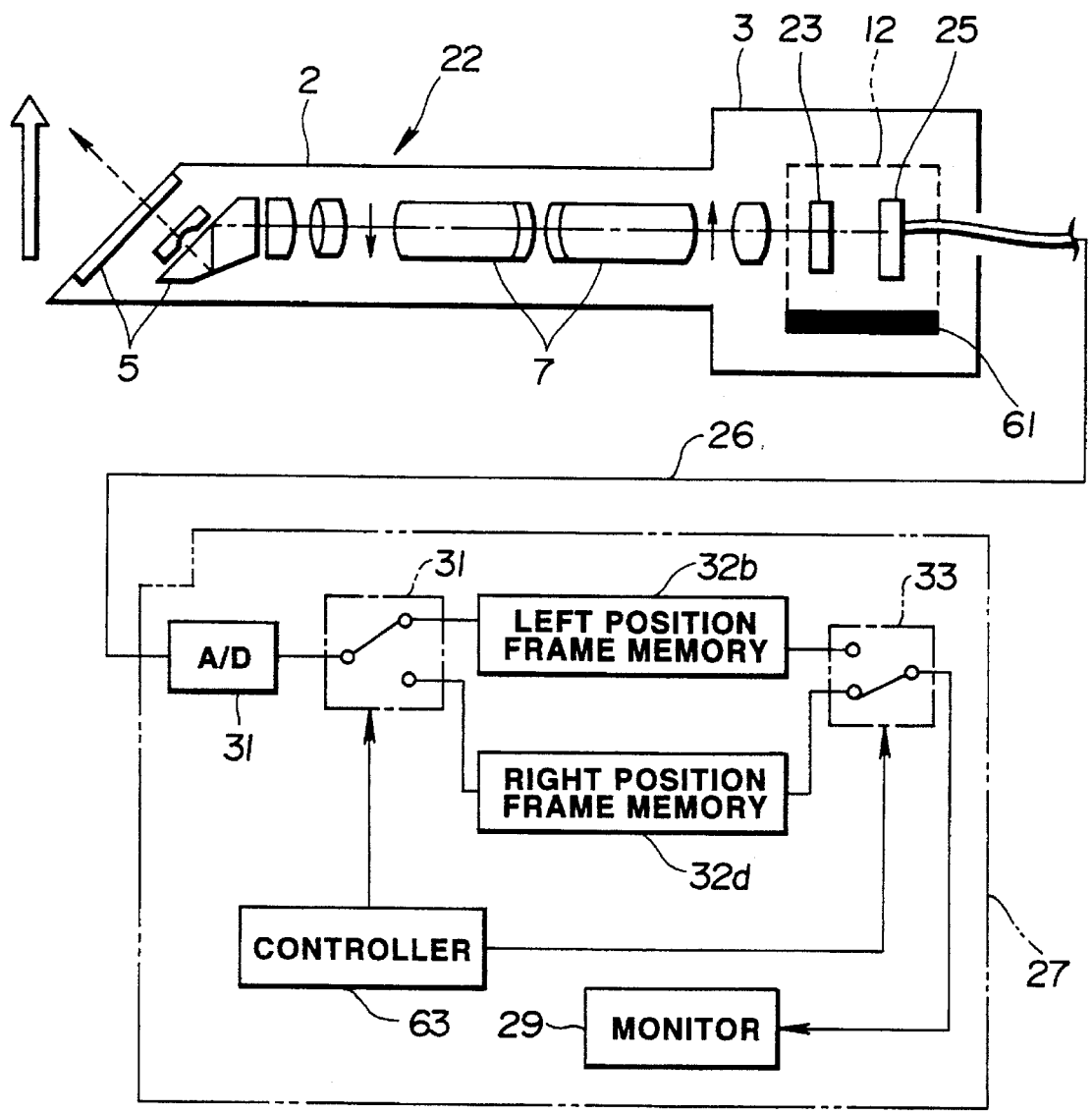

As shown in FIG. 7, in the stereoscopic rigid-type endoscope of this embodiment, the pupil dividing shutter 23 and the CCD 25 are arranged inside the rotation section 12, in the optical axis of the relay lens system 7, which is rotatable around this optical axis. Since, as stated above, the weight 61 is secured to the rotating section 12, the pupil dividing shutter 23 and the CCD 25 are constantly secured in position with respect to the gravitational dimension.

The CCD 25 of this embodiment is electrically connected through a signal line 26 to a controller 27, which is substantially the same as the controller in the second embodiment. Thus, as shown in FIGS. 8 and 9, the right and left images are formed on the CCD through the shutter hole 23a, and the image sensing signals output from the CCD 25 are subjected to signal processing to display an image which can be stereoscopically observed on a monitor 29.

The left and right images transmitted through the shutter hole 23a of the pupil dividing shutter 23 are stored in a left frame memory 32b and a right frame memory 32d, respectively, and the image signals stored in these frame memories are alternately read for display on the monitor screen.

Due to the above-described construction, in which a weight is secured to the rotating section rotatable around the optical axis and in which the pupil dividing shutter and the CCD are arranged in the optical axis of the relay lens system, it is possible for the pupil dividing shutter and the CCD to be constantly held in the proper position with respect to the gravitational dimension even if the endoscope is rotated.

In this embodiment, it is possible to provide a gravitation detecting means, instead of the weight. By controlling the rotating means on the basis of a bottom dimension as detected by the gravitation detecting means, the bottom dimension of the image displayed on the monitor screen can be automatically made coincident with the actual bottom (gravitational) dimension.

Further, it is possible not only to make the monitor bottom dimension coincident with the gravitational dimension, but also to effect display with the observer's orientation arbitrarily set, for example, in accordance with the positional relationship between the observer and the monitor, depending upon the condition in which the endoscope is used.

The other effects and advantages of this embodiment are the same as those in the previous embodiments.

Here, another embodiment of the pupil dividing shutter will be described.

Figure 10:
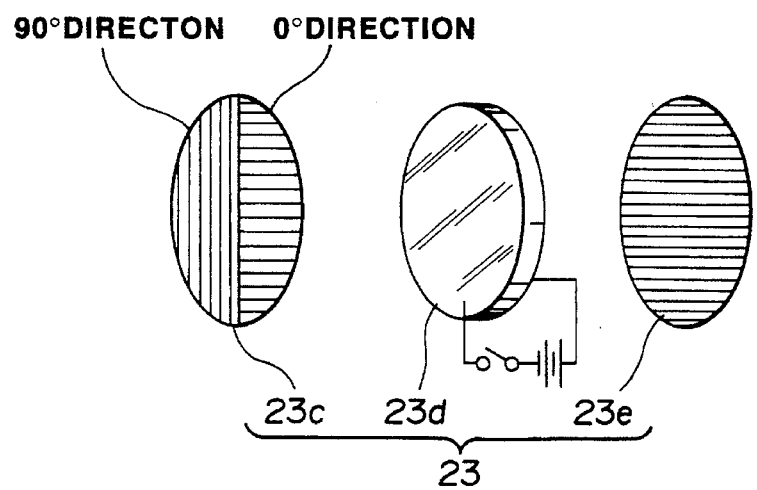
FIG. 10 shows another example of the pupil dividing shutter.

FIG. 10 shows a pupil dividing shutter which consists of a combination of polarizing plates and a liquid Crystal cell. As shown in the drawing, this pupil driving shutter comprises: a polarizing plate 23c which constitutes a first polarizing means and which is composed of right and left polarizing plate sections whose respective polarizing directions intersect each other, for example, one in 0° direction and the other in 90° direction; a liquid crystal cell 23d constituting a plane-of-polarization turning means having the function to turn the plane of polarization of the incident light; and a polarizing plate 23e which constitutes a second polarizing means and whose polarizing direction is the same as one of the polarizing directions of the polarizing plate 23c. By controlling the voltage applied to the liquid crystal cell 23d, switching is effected between the state in which the light incident on the liquid crystal cell 23d is output as it is and the state in which the plane of polarization of the incident light is turned by 90° before the light is output. Due to this arrangement, light which has been transmitted through only one of the polarizing plate sections, one in 0° direction and the other in 90° direction, of the polarizing plate 23c is output from the polarizing plate 23e, thereby effecting pupil division.

Figure 11:
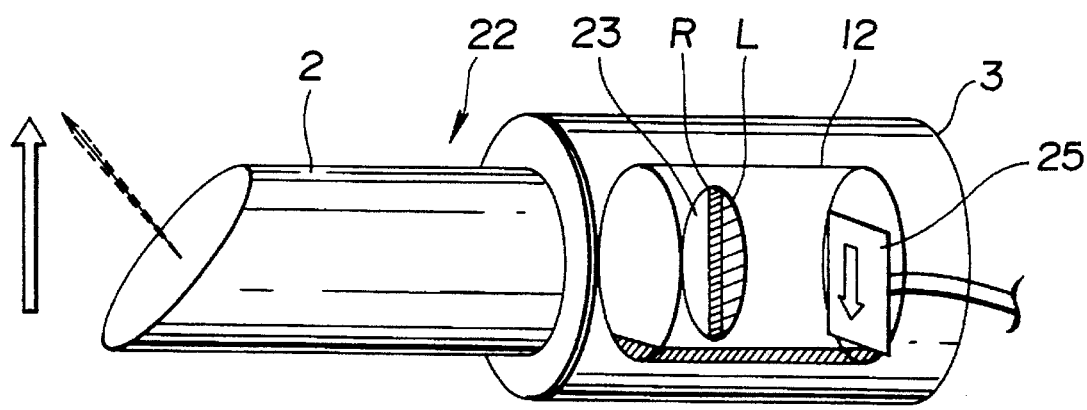
FIG. 11 shows the pupil dividing shutter of FIG. 10 arranged in a stereoscopic oblique-view-type endoscope.
Figure 12:
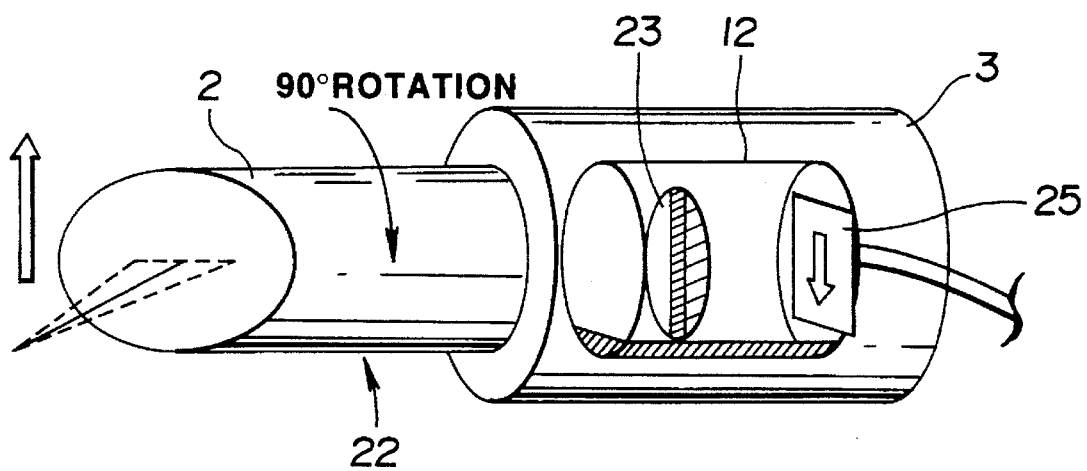
FIG. 12 shows the stereoscopic oblique-view-type endoscope of FIG. 11 rotated by 90°.

FIGS. 11 and 12 show a stereoscopic rigid-type endoscope of an oblique-view type which is provided with the above-described pupil dividing shutter. Due to the rotating section 12 having the weight 61, the pupil dividing shutter 23 and the CCD 25 of this stereoscopic rigid-type endoscope of the oblique-view type can be held in the proper position with respect to the gravitational dimension, as in the case of the stereoscopic rigid-type endoscope of the third embodiment, even if the endoscope 22 is rotated.

Thus, the top-to-bottom relationship of the endoscopic image displayed on the monitor screen is not changed with the rotation of the endoscope.

Further, since the position of the CCD 25 is also free from rotation and constantly kept stationary, the cable 26 extending from the CCD 25 to the exterior is prevented from being twisted.

Figure 13A:
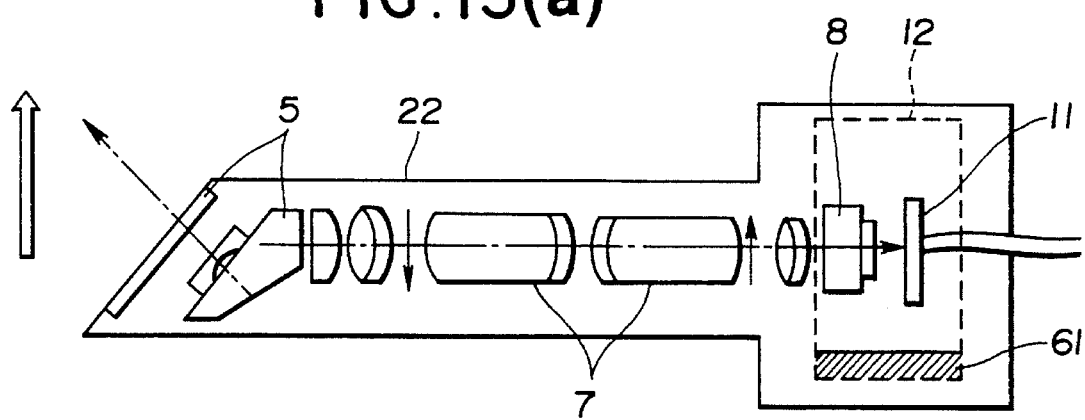
FIGS. 13(a) and 13(b) shows the construction of a stereoscopic rigid-type endoscope according to a fourth embodiment of the present invention.
Figure 13B:
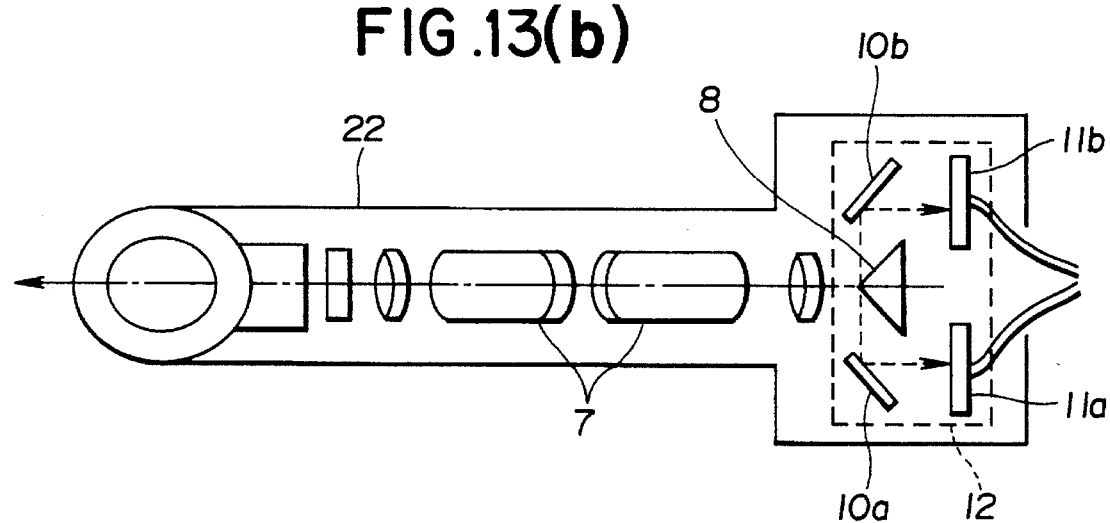

FIG. 13 shows a stereoscopic rigid-type endoscope 22 of the oblique-view type according to the fourth embodiment of this invention. In contrast with the embodiment shown in FIG. 1, the fourth embodiment employs a construction in which the weight 61 is fastened to the rotating section 12, as in the embodiment shown in FIG. 7.

Since the weight, which keeps the rotating section stationary with respect to the gravitational dimension, is fastened to the rotating section, the image sensing section is prevented from rotating with respect to the gravitational dimension as in the third embodiment even when the endoscope rotates, so that the image displayed on the monitor is free from rotation.

Figure 14:
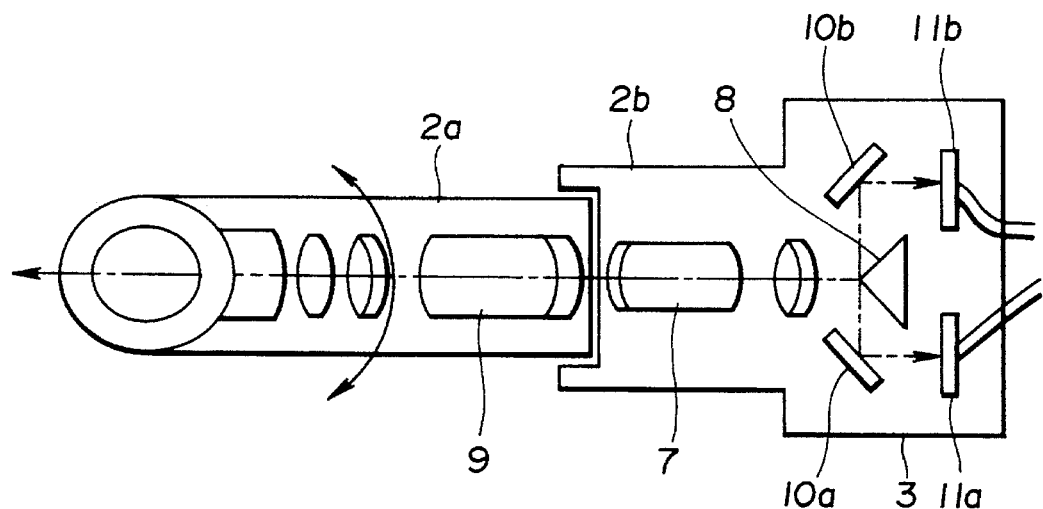
FIG. 14 shows the construction of a stereoscopic rigid-type endoscope according to a fifth embodiment of the present invention.

FIG. 14 shows a stereoscopic rigid-type endoscope 22 according to the fifth embodiment of this invention. In contrast with the embodiment shown in FIG. 1, the fifth embodiment adopts a construction in which, instead of providing the rotating section, the inserting section 2 of the endoscope 22 is separated into front and rear sections 2a and 2b, which are capable of rotating relative to each other around the optical axis of the relay lens system 7, that is, of the endoscope optical system.

In accordance with this embodiment, the operator can hold the operating/holding section 3, connected with the rear section 2b of the inserting section 2 and containing the image sensing system, rotating the front section 2a of the inserting section while keeping the operating/holding section 3 stationary with respect to the gravitational dimension.

Figure 15:
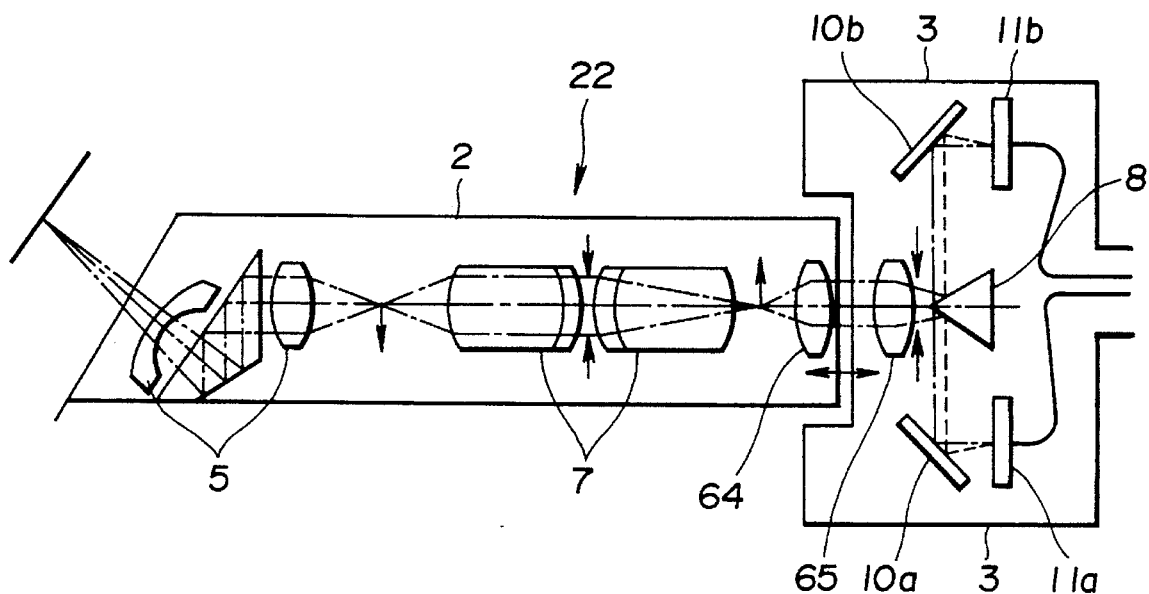
FIG. 15 shows the construction of a stereoscopic rigid-type endoscope according to a modification of the fifth embodiment.

FIG. 15 shows a modification of the embodiment of FIG. 14. In this modification, the inserting section 2 and the operating/holding section 3 are separated and rotatable relative to each other around the optical axis of the endoscope optical system. Further, in this modification, lenses 64 and 65 are arranged at the rear end of the inserting section 2 and the front end of the operating/holding section 3, respectively, converting the light flux in the joint section (rotary section) between the inserting section 2 and the operating/holding section 3 into a parallel ray.

Thus, with this modification, it is possible to prevent the image from deteriorating even if there is some play along the longitudinal dimension of the rotary section.

Figure 16:
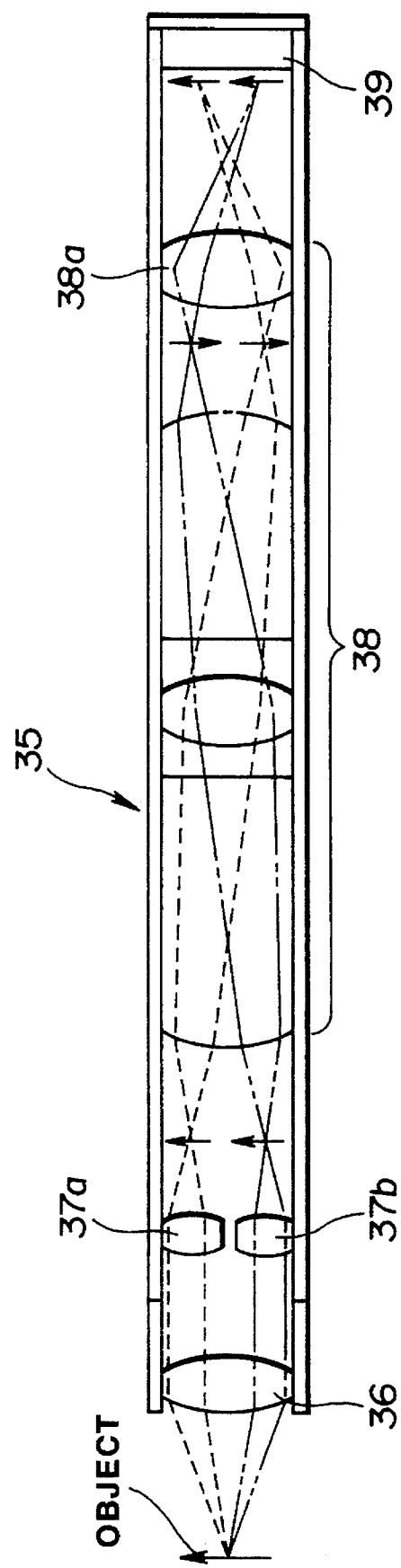
FIG. 16 is a sectional view showing the construction of another stereoscopic endoscope which makes stereoscopic observation possible.

FIG. 16 shows a stereoscopic rigid-type endoscope 35 which contains in its rigid, thin and narrow inserting section: an objective lens 36; image forming lenses 37a and 37b having a diameter smaller than that of the objective lens 36; a relay lens section 38 composed of a plurality of lenses for separately transmitting two images formed by two image forming lenses 37a and 37b, respectively; and a CCD 39 for picking up an image formed by an image forming lens 38a located at the rearmost end of the relay lens section 38, the above components being arranged in that order from the front end of the inserting section. Like the above-described stereoscopic endoscopes, the stereoscopic rigid-type endoscope 35 is designed to obtain left and right images by pupil division.

Light from the object to be observed is transmitted partly through the objective lens 36 and the image forming lens 37a and partly through the objective lens 36 and the image forming lens 37b to form two images, divided with respect to the optical axis, behind these image forming lenses 37a and 37b, which are shaded by a shading member (not shown) so as to be optically separated from each other in order that the image transmitted through one image forming lens may not be formed with the one transmitted through the other lens.

The two images formed by the image forming lenses 37a and 37b are transmitted rearwards through the relay lens section 38 to form two images having parallax on the CCD 39. As in the above embodiments, the electric signals output from the CCD 39 undergo signal processing and are displayed on a monitor, enabling the viewer to stereoscopically observe the object.

Since the stereoscopic rigid-type endoscope 35 comprises a single line of optical system, there is only a remote possibility that there is a disparity between the left and right images. Further, it is less expensive than endoscopes having two lines of optical systems.

Figure 17:
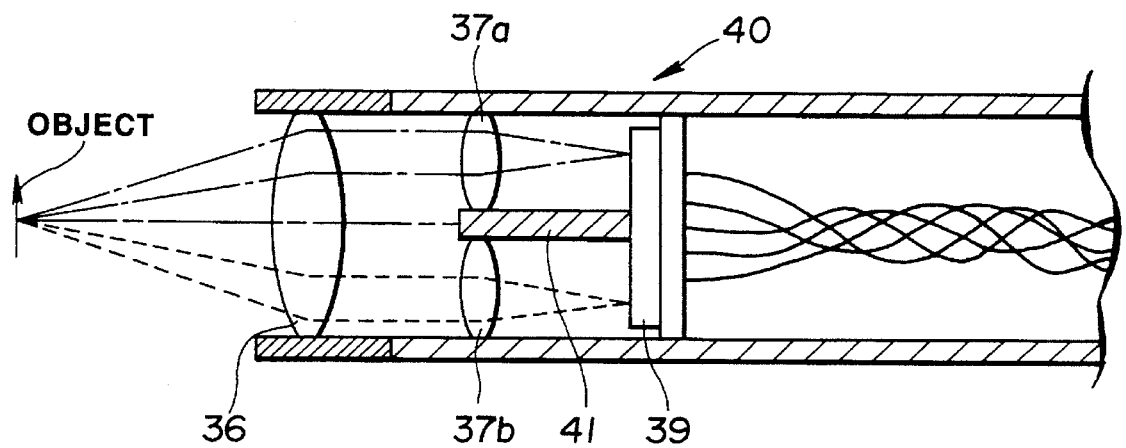
FIG. 17 is a sectional view showing the construction of still another stereoscopic endoscope which makes stereoscopic observation possible.
Figure 18:
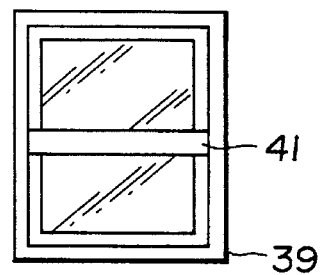
FIG. 18 is a front view of the solid-state image sensing device of FIG. 17.

FIGS. 17 and 18 show a stereoscopic rigid-type endoscope 40 which is formed by removing the relay lens section 38 from the endoscope 35 shown in FIG. 16 and arranging a CCD 39 in the front end section thereof. Provided between the image forming lenses 37a and 37b is a shading member 41, which extends up to the surface of the CCD 39.

The other structural features and effects of the stereoscopic rigid-type endoscope 40 are the same as those of the one shown in FIG. 16, so a description thereof will be omitted.

FIGS. 19(a) and 19(b) show a stereoscopic rigid-type endoscope 43 which includes, for stereoscopic observation, two relay optical systems 44a and 44b and a pair of CCDs 45a and 45b serving as the image sensing means for picking up images transmitted through the relay optical systems 44a and 44b.

The stereoscopic rigid-type endoscope 43 comprises a rigid inserting section 46, and an operating/holding section 47 having a relatively large diameter and joined with the inserting section 46. The relay optical systems 44a and 44b, contained in the inserting section 46, are shaded from each other by a shading member (not shown).

The operating/holding section 47 is composed of a cover member 47a on the front end side and a holding section body 47b, which are separated from each other to be detachably engaged by a screwing means or the like. Further, a protruding section on the back side of the holding section body 47b is detachably engaged with a rear member 47c by a screwing means. A cable protector 49 made of a plastic material or the like is provided at the rear end of the rear member 47c so as to cover a cable 48. Further, provided between the cover member 47a and the holding section body 47b is a sealing member 47d for keeping the inner space, defined by the screwing engagement of the cover member 47a with holding section body 47b, watertight.

Arranged inside the cover member 47a of the operating/holding section 47 is a prism 50 for reflecting the images, transmitted through the relay optical systems 44a and 44b, in directions each perpendicular to the optical axis. Further, the cover member 47a of the operating/holding section 47 contains mirrors 51a and 51b for reflecting the two images, reflected by the prism 50, in directions parallel to the optical axes of the relay optical systems, and image forming lenses 52a and 52b for forming the images reflected by the mirrors 51a and 51b.

The holding section body 47b of the operating/holding section 47 has a cover glass 53 near its front opening. Further, the holding section body 47b contains CCDs 45a and 45b for picking up the two images formed by the image forming lenses 52a and 52b. Image sensing peripheral circuits 58a and 58b are provided at the rear end of the CCDs 45a and 45b.

The CCDs 45a and 45b pick up the images having parallax, transmitted through the two relay optical systems, and converts them to electric signals, which are supplied to the controller. The signal processing for stereoscopic observation is the same as that in the above embodiments, so a description thereof will be omitted.

In the stereoscopic rigid-type endoscope 43 shown in FIG. 19(a), the optical systems and the CCDs are detachable with respect to each other. Further, since the optical systems and the CCDs can be formed as an integral unit, the stereoscopic rigid-type endoscope 43 excels in operability.

The optical axes of the relay optical systems, contained in the endoscope inserting section, are bent by a prism and mirrors constituting an optical path changing means so as to be adapted to the size of the CCDs. Therefore, the stereoscopic rigid-type endoscope 43 can use large CCDs having high resolution.

It is desirable for the diameter of the endoscope inserting section to be reduced so as attain an improvement in insertion property. In view of this, in this stereoscopic endoscope, the optical path changing means is provided in the operating/holding section, whose diameter may be relatively large, and, at the optical path is made coincident with the optical axes of the two CCDs.

Although this embodiment has been described with reference to a structure in which two relay optical systems are arranged inside the endoscope inserting section, it goes without saying that it is also applicable to a structure in which, as in the above embodiments, one relay optical system is arranged inside the endoscope inserting section.

FIG. 19(b) shows a stereoscopic rigid-type endoscope 54 formed by partly modifying the endoscope shown in FIG. 19(a). In the stereoscopic rigid-type endoscope 54, the optical path changing means for bending the optical axes of the relay optical systems is provided on the image sensing side, that is, in the holding section body 47b. Arranged on the inside of the cover glass 53 are a prism 55 for bending the optical axes of the relay optical systems 44a and 44b in such a way as to diverge them, i.e., obliquely, and image forming lenses 57a and 57b for forming images of the object on the CCDs 56a and 56b. Thus, the image areas of the CCDs 56a and 56b are oblique with respect to the optical axes of the relay optical systems.

The other structural features and effects of this endoscope are the same as those of the endoscope 43 shown in FIG. 19(a), and the components thereof which are the same as those of the endoscope 43 will be referred to by the same reference numerals, a description of such components being omitted.

In the endoscope 43 shown in FIG. 19(a), the optical path changing means may be provided on the image sensing side. In the endoscope 54 shown in FIG. 19(b), the optical path changing means for obliquely bending the optical path may be provided on the optical system side in order to secure the requisite space.

It is obviously possible for the present invention to be embodied in forms varying in a wide range without departing from the spirit and scope thereof. The scope of the present invention, therefore, is determined solely by the appended claims and not limited by any specific embodiments thereof.

What is claimed is:

1. A stereoscopic endoscope having an inserting section comprising:

an image forming optical system arranged in an inserting section of the endoscope and provided with a single objective lens system at a distal end of the inserting section for forming an object image, and an image transmission means including a relay lens system for reforming said object image, said objective lens system and said relay lens system having a common optical axis;

pupil dividing shutter means for selectively making different areas of a pupil of said image forming optical system transmittable by receiving light transmitted through said relay lens system;

a single image sensing means for receiving images formed by light fluxes transmitted through said pupil dividing shutter means;

a first support means for supporting at least said objective lens system; and a second support means for supporting at least said image sensing means, said first and second support means each being independently rotatable relative to each other around an axis extending along the longitudinal dimension of the endoscope.

2. A stereoscopic endoscope according to claim 1, further including a visual-field direction deviation means for deviating the visual-field direction of the endoscope in a direction other than from the longitudinal dimension thereof.

3. A stereoscopic endoscope according to claim 1, wherein said inserting section containing said objective lens system and said image transmission means is divided into front and rear inserting-section parts which are rotatable relative to each other around the optical axis of the optical system.

4. A stereoscopic endoscope having an inserting section comprising:

an image forming optical system arranged in an inserting section of the endoscope and provided with a single objective lens system at a distal end of the inserting section for forming an object image, and an image transmission means including a relay lens system for reforming said object image, said objective lens system and said relay lens system having a common optical axis;

pupil dividing shutter means for selectively making different areas of a pupil of said image forming optical system transmittable by receiving light transmitted through said relay lens system; and a single image sensing means for receiving images formed by light fluxes transmitted through said pupil dividing shutter means, wherein said pupil dividing shutter means consists of a plate member rotating around an axis of rotation parallel to the optical axis of said image forming optical system, said plate member including an opening at a position spaced apart from the axis of rotation thereof, said opening being provided at a position which is constantly illuminated by the light flux which is outputted from said relay lens system even if said plate member is rotated.

5. A stereoscopic endoscope according to claim 4, further comprising control means for obtaining output signals from said image sensing means in synchronism with the operation of said pupil dividing shutter means.

6. A stereoscopic endoscope according to claim 5, further comprising an A/D converter for A/D-converting electric signals supplied to said control means from said image sensing means; a change-over switch for distributing the output signals from said A/D converter; frame memories each storing, frame by frame, the output signals distributed by said change-over switch; and change-over switches for alternately reading the signals stored in said frame memories.

7. A stereoscopic endoscope, comprising:

an image forming optical system arranged in an inserting section of the endoscope and provided with a single objective lens system at a distal end of the inserting section and a relay lens system for relaying an image formed by said objective lens, said objective lens system and said relay lens system having a common optical axis;

a first support means for supporting at least said objective lens system;

pupil dividing shutter means for selectively making different areas of a pupil of said image forming optical system transmittable;

a single image sensing means for receiving images formed by light fluxes transmitted through said pupil dividing shutter means; and a second support means for supporting at least said image sensing means, said first and second support means each being independently rotatable relative to each other around an axis extending along the longitudinal dimension of the endoscope, wherein a weight for stabilization with respect to a gravitational dimension is fastened to the second support means to which said pupil dividing shutter means and said image sensing means are secured.

8. A stereoscopic endoscope comprising:

an image forming optical system arranged in an inserting section of the endoscope and provided with a single objective lens system at a distal end of the inserting section and a relay lens system for relaying an image formed by said objective lens, said objective lens system and said relay lens system having a common optical axis;

a first support means for supporting at least said objective lens system;

pupil dividing shutter means for selectively along different areas of a pupil of said image forming optical system transmittable;

a single image sensing means for receiving images formed by light fluxes transmitted through said pupil dividing shutter means; and a second support means for supporting at least said image sensing means, said first and second support means each being independently rotatable relative to each other around an axis extending along the longitudinal dimension of the endoscope, wherein said pupil dividing shutter means comprises:
    a first polarizing means composed of two polarizing plate sections arranged side by side and having different directions of polarization;
    a plane-of-polarization turning means capable of turning the polarization plane of incident light; and
    a second polarizing means consisting of a unitary polarizing plate, said first polarizing means, said plane-of-polarization turning means and said second polarizing means being arranged in that order along the optical axis.

9. A stereoscopic endoscope having an inserting section comprising:

an image forming optical system arranged in an inserting section of the endoscope and provided with a single objective lens system at a distal end of the inserting section for forming an object image, and an image transmission means including a relay lens system for reforming said object image, said objective lens system and said relay lens system having a common optical axis;

pupil dividing shutter means for selectively making different areas of a pupil of said image forming optical system transmittable by receiving light transmitted through said relay lens system;

a single image sensing means for receiving images formed by light fluxes transmitted through said pupil dividing shutter means;

a first support means for supporting at least said objective lens system; and a second support means for supporting at least said image sensing means, said first and second support means each being independently rotatable relative to each other around an axis extending along the longitudinal dimension of the endoscope, wherein said endoscope is separated into said inserting section supported by said first support means containing said objective lens system and said image transmission means and an operating/holding section supported by said second support means containing said pupil dividing shutter means and said image sensing means for picking up object images obtained by said pupil dividing means, said inserting section and said operating/holding section being rotatable relative to each other around the optical axis of the optical system.

10. A stereoscopic endoscope having an inserting section comprising:

an image forming optical system arranged in an inserting section of the endoscope and provided with a single objective lens system at a distal end of the inserting section for forming an object image, and an image transmission means including a relay lens system for reforming said object image, said objective lens system and said relay lens system having a common optical axis;

pupil dividing shutter means for selectively making different areas of a pupil of said image forming optical system transmittable by receiving light transmitted through said relay lens system; and a single image sensing means for receiving images formed by light fluxes transmitted through said pupil dividing shutter means, wherein said inserting section is elongated for insertion into a narrow area, said inserting section containing said objective lens system and said image transmission means, said pupil dividing shutter means being provided external to said inserting section, said pupil dividing shutter means and said inserting section being rotatable relative to each other around the optical axis of said image transmission means as a rotation axis.

11. A stereoscopic endoscope according to claim 10, wherein said pupil dividing shutter means and said image sensing means are arranged in fixed positions relative to each other.

12. A stereoscopic endoscope according to claim 10, wherein said pupil dividing shutter means and said image sensing means are rotatably arranged relative to each other around said rotation axis.

13. A stereoscopic endoscope according to having an inserting section comprising:

an image forming optical system arranged in an inserting section of the endoscope and provided with a single objective lens system at a distal end of the inserting section for forming an object image, and an image transmission means including a relay lens system for reforming said object image, said objective lens system and said relay lens system having a common optical axis;

pupil dividing shutter means for selectively making different areas of a pupil of said image forming optical system transmittable by receiving light transmitted through said relay lens system; and a single image sensing means for receiving images formed by light fluxes transmitted through said pupil dividing shutter means;

a first support means for supporting at least said objective lens system; and a second support means for supporting at least said image sensing means, said first and second support means each being independently rotatable relative to each other around an axis extending along the longitudinal dimension of the endoscope, wherein said pupil dividing shutter means is supported by said second support means.

14. A stereoscopic endoscope comprising:

an image forming optical system arranged in an inserting section of the endoscope and provided with a single objective lens system at a distal end of the inserting section and a relay lens system for relaying an image formed by said objective lens, said objective lens system and said relaying lens system having a common optical axis;

pupil dividing shutter means for selectively making different areas of a pupil of said image forming optical system transmittable; and a single image sensing means for receiving images formed by light fluxes transmitted through said pupil dividing shutter means, wherein said pupil dividing shutter means comprises:

a first polarizing means composed of two polarizing plate sections arranged side by side and having different directions of polarization;

a plane-of-polarization turning means capable of turning the polarization plane of incident light; and a second polarizing means consisting of a unitary polarizing plate, said first polarizing means, said plane-of-polarization turning means and said second polarizing means being arranged in that order along the optical axis.

\* \* \* \* \*